(12) United States Patent
Shuster et al.

(10) Patent No.: US 12,390,604 B2
(45) Date of Patent: Aug. 19, 2025

(54) DEVICES FOR VAPORIZATION OF COMPOUNDS COMPRISING AN OXYGEN DETECTION MECHANISM UPSTREAM OF THE VAPORIZATION CHAMBER AND VAPORIZATION DEVICE WITH CHOPPING ELEMENT INTERNAL TO THE VAPORIZATION CHAMBER

(71) Applicants: Gary Stephen Shuster, Vancouver (CA); Brian Shuster, Vancouver (CA)

(72) Inventors: Gary Stephen Shuster, Vancouver (CA); Brian Shuster, Vancouver (CA)

( * ) Notice: Subject to any disclaimer, the term of this patent is extended or adjusted under 35 U.S.C. 154(b) by 9 days.

(21) Appl. No.: 17/833,733

(22) Filed: Jun. 6, 2022

(65) Prior Publication Data
US 2022/0296824 A1  Sep. 22, 2022

Related U.S. Application Data

(63) Continuation of application No. 16/324,536, filed as application No. PCT/IB2017/001136 on Aug. 10, 2017, now Pat. No. 11,351,315.
(Continued)

(51) Int. Cl.
*A61M 11/04* (2006.01)
*A24F 1/02* (2006.01)
(Continued)

(52) U.S. Cl.
CPC .............. *A61M 11/042* (2014.02); *A24F 1/02* (2013.01); *A24F 7/00* (2013.01); *A24F 9/12* (2013.01);
(Continued)

(58) Field of Classification Search
CPC .. A61M 11/042; A61M 15/06; A61M 15/002; A61M 15/0021; A61M 15/0088;
(Continued)

(56) References Cited

U.S. PATENT DOCUMENTS

2006/0231091 A1* 10/2006 Camarillo ............. A61M 16/06
128/200.21
2007/0101994 A1*  5/2007 Waters ............... A61M 16/0833
128/205.12
(Continued)

*Primary Examiner* — Xiao S Zhao
*Assistant Examiner* — Guy F Mongelli
(74) *Attorney, Agent, or Firm* — Sherrie M. Flynn; Aisha O. Otori; Coleman & Horowitt LLP

(57) ABSTRACT

Systems, methods and apparatuses for vaporizing all or substantially all plant matter, liquid and/or other material to be vaporized are disclosed. Embodiments of the invention comprise a vaporization chamber sealed except for at least two conduits, heating element, a first conduit coupled to a source of fully or almost fully non-oxygenated gas, a heating element capable of heating the vaporization chamber to a temperature above a combustion temperature, a second conduit configured to transport vaporization gases and vaporized elements out of the vaporization chamber and at least one valve positioned in the second conduit preventing the flow of atmospheric air into the vaporization chamber. In some instances, the first gas substantially clears the vaporization chamber of atmospheric air prior to reaching combustion temperature. A second gas containing oxygen may be intermixed with the vaporization gases and vaporized elements proximal to the combustion chamber.

17 Claims, 4 Drawing Sheets

Related U.S. Application Data

(60) Provisional application No. 62/384,658, filed on Sep. 7, 2016, provisional application No. 62/377,001, filed on Aug. 19, 2016, provisional application No. 62/373,185, filed on Aug. 10, 2016.

(51) Int. Cl.
| | | |
|---|---|---|
| *A24F 7/00* | (2006.01) | |
| *A24F 9/12* | (2006.01) | |
| *A24F 40/20* | (2020.01) | |
| *A24F 40/46* | (2020.01) | |
| *A24F 40/485* | (2020.01) | |
| *A24F 40/53* | (2020.01) | |
| *A61M 15/00* | (2006.01) | |
| *A61M 15/06* | (2006.01) | |
| *F25B 21/04* | (2006.01) | |

(52) U.S. Cl.
CPC ............ *A24F 40/46* (2020.01); *A24F 40/485* (2020.01); *A24F 40/53* (2020.01); *A61M 15/06* (2013.01); *F25B 21/04* (2013.01); *A24F 40/20* (2020.01); *A61M 15/002* (2014.02); *A61M 15/0021* (2014.02); *A61M 15/0088* (2014.02); *A61M 2202/025* (2013.01); *A61M 2205/18* (2013.01); *A61M 2205/3306* (2013.01); *A61M 2205/3368* (2013.01); *A61M 2205/3375* (2013.01); *A61M 2205/3606* (2013.01); *A61M 2205/3673* (2013.01); *A61M 2205/582* (2013.01); *A61M 2205/583* (2013.01)

(58) Field of Classification Search
CPC ........ A61M 2202/025; A61M 2205/18; A61M 2205/3306; A61M 2205/3368; A61M 2205/3375; A61M 2205/3606; A61M 2205/3673; A61M 2205/582; A61M 2205/583; A24F 1/02; A24F 7/00; A24F 9/12; A24F 40/46; A24F 40/485; A24F 40/53; A24F 40/20; F25B 21/04
See application file for complete search history.

(56) References Cited

U.S. PATENT DOCUMENTS

| | | | |
|---|---|---|---|
| 2008/0149118 A1* | 6/2008 | Oglesby | A24F 42/10 131/194 |
| 2011/0192399 A1* | 8/2011 | Wilke | A61M 11/041 392/390 |
| 2013/0104888 A1* | 5/2013 | Landis | A61M 16/142 128/203.26 |
| 2013/0247905 A1* | 9/2013 | Miller | A61M 16/20 128/201.13 |
| 2015/0027204 A1* | 1/2015 | Stoks | G01F 23/26 73/31.05 |

* cited by examiner

DEVICES FOR VAPORIZATION OF COMPOUNDS COMPRISING AN OXYGEN DETECTION MECHANISM UPSTREAM OF THE VAPORIZATION CHAMBER AND VAPORIZATION DEVICE WITH CHOPPING ELEMENT INTERNAL TO THE VAPORIZATION CHAMBER

CROSS-REFERENCE TO RELATED APPLICATIONS

This application claims priority to and is a continuation of U.S. patent application Ser. No. 16/324,536, filed Feb. 8, 2019, which will issue as U.S. Pat. No. 11,351,315 on Jun. 7, 2022, which, pursuant to 35 U.S.C. § 371, is a U.S. National Phase application of and claims priority to PCT/IB2017/001136 filed Aug. 10, 2017, which claims priority pursuant to 35 U.S.C. § 119(e) to U.S. Provisional Patent Application Nos. 62/373,185 filed Aug. 10, 2016, 62/377,001 filed Aug. 19, 2016 and 62/384,658 filed Sep. 7, 2016. The text and contents of each of these patent applications are hereby incorporated into this application by reference as though fully set forth herein.

BACKGROUND

1. Field

The present disclosure relates to vaporization and/or aerosolization of plant matter or other materials.

2. Description of Related Art

Vaporization, the conversion of a substance from the liquid or solid phase into a gaseous or vapor phase, has seen growing adoption as a way to inhale physiologically and/or psychologically active compounds without inhaling byproducts of combustion. For example, tobacco leaves heated to 140-200° C. will aerosolize certain of the organic compounds in the tobacco leaves, allowing inhalation without also inhaling combustion byproducts.

Vaporizers are also used to release scents from plants, flavors and scents from spices, and for other purposes. One growing use of vaporizers is for the consumption of medical *cannabis*. Certain studies, such as a 2007 study by University of California, San Francisco and published in the Journal of the American Academy of Neurology, have found substantial safety benefits from the use of a vaporizer when compared to combustion. As that study states, "there was virtually no exposure to harmful combustion products using the vaporizing device."

However, there are several problems with vaporizing. A primary problem is that plant matter heats unevenly in a vaporizer. Unlike a combustion device, a vaporizer may leave the structure of the plant matter intact (whereas combustion turns it to ash). As a result, it is important to grind the plant matter into small pieces in order to minimize the amount of organic matter trapped inside of plant structure and to allow more even heating. However, there is a maximum amount of grinding that is possible before the matter becomes small enough to pass through any filters or grates. Put another way, vaporizing will always leave some amount of organic matter non-aerosolized.

Another problem with vaporizers is that the heat source is frequently inconsistent. For example, some vaporizers use resistance heating, creating hot spots near the wires. Others use passive-convection, with differing amounts of heat passing through differing parts of the apparatus. One of the side effects of vaporizing is that liquid present in the plant matter evaporates, changing the susceptibility of the remaining plant matter to combustion. It is thus desirable to change vaporizing temperature as the matter dries out. Regardless, it is common for vaporizing at higher temperatures to result in some amount of combustion. Further, while combustion is a rapid means of oxidation, it should be appreciated that certain organic compounds combine with oxygen at lower temperatures.

Yet another problem with both combustion and vaporization technology is that the odor of heated plant matter is often quite noticeable.

With regard specifically to vaporization of *cannabis*, it should be understood that Tetrahydrocannabinolic acid (THCA) is the biosynthetic precursor to the psychoactive tetrahydrocannabinol (THC). THCA has no known psychoactive effects on humans, although there is research showing significant medical impacts of THCA, such as anti-inflammatory and antiemetic properties. Heating THCA causes substantial conversion to THC, whereas ingestion of THCA leads to a highly limited amount of in vivo conversion to THC. A failure to sufficiently heat the THCA may lead to incomplete conversion of the totality of THCA within the plant matter. Further, one of the reasons why *cannabis* needs to be dried prior to use is to further the conversion of THCA to THC.

Fire is an exothermic chemical process of combustion leading to rapid oxidation of a material. A popular additive to e-cigarettes is propylene glycol/glycerin. Propylene glycol may degrade in the presence of oxygen. Any combustion process will lead to undesirable chemicals. Indeed, even a hypothetical fully efficient combustion process will result in at least the creation of carbon dioxide, a substance that is undesirable for inhalation.

Returning to the problem of uneven distribution of heat in vaporization, a workaround that is only partially effective is to break the plant matter into very small pieces. Similarly, with liquid vaporization, thermally conductive materials may be used. However, even a slightly uneven heat distribution may lead to some areas of material being vaporized, others not vaporized, and yet other areas being burned or combusted. In addition, substances prepared for vaporization in a non-naturally occurring form, such as in an oil suspension, are frequently extracted utilizing undesirable chemicals, and may additionally contain substances that are undesirable to inhale. As carbon dioxide, carbon monoxide and other undesirable and/or harmful combustion byproducts combine atmospheric oxygen with product intended for vaporization, there is an upper temperature limit for vaporization in order to avoid combustion. However, at this upper limit, there is still insufficiently even heating to efficiently vaporize all of the material.

Existing vaporization technology is insufficient to address these issues. One exemplary existing vaporizer is the Bronze Sherlock VG Vaporizer (http://vaporgenie.com/bronze-sherlock-vaporizer). It is described as working as follows: "The VaporGenie pipe has a ceramic filter in the sphere above the bowl. The ceramic filter is designed to thoroughly mix heat from flame with cold, ambient air, producing an air stream with a temperature of about 275-350° F. This air stream is hot enough to vaporize plant essences, but not hot enough to burn." As noted above, this temperature will only vaporize a portion of the desired "plant essences".

Other vaporizers use internal heating elements may be found at http://www.mrniceguyheadshops.com/blog/2014/12/22/vaping-what-is-it-best-vaporizers.

Additionally, a popular vaporizer is the "Volcano, which may be found at http://www.volcanovape.net/.

The Volcano Vaporizer utilizes a vacuum system that pumps in fresh, filtered air, which is heated to temperatures needed for vaporization. Hot air passes over aromatic blends or essential oils to create vapor, filling the Volcano balloon by method of forced air. Once the balloon is filled with vapor, it is ready to be detached and used (see also: http://www.vapeworld.com/volcano-vaporizer-blazing).

SUMMARY

It is desirable to provide a system, method, and apparatus for vaporizing all or substantially all plant matter and/or liquid and/or other material to be vaporized (this grouping of all vaporization targets is referenced herein as "Vaporization Targets" and include each of the foregoing unless the context requires otherwise).

For ease of discussion, the portion of the device between the vaporization chamber and the mouthpiece is sometimes referenced as the "proximal" portion of the device, while the portion of the device between the vaporization chamber and the non-oxygenated gas source is sometimes referenced as the "distal" portion of the device.

The instant inventions utilize one or more of, among other things, a heating element, a heating chamber, a power source, a source of gas other than oxygen or O2 (for example, helium, argon, or nitrogen), a cooling mechanism (which may simply be piping or may be more complex) and a delivery system (whether direct delivery, such as a mouthpiece, or delayed delivery, such as storing the output in a balloon or sealed container).

In one aspect, it should be noted that it is desirable to utilize a gas (or combination of gasses) that is lighter than air, as there is a risk of asphyxiation if one inhales a gas that is significantly heavier than air.

It is to be understood that both the foregoing general description and the following detailed description are exemplary, but not restrictive, of the invention. A more complete understanding of the improved solar collector and the methods disclosed herein will be afforded to those skilled in the art.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications, and equivalents that may be included within the spirit and scope of the invention. Furthermore, in the following detailed description of the present invention, numerous specific details are set forth in order to provide a thorough understanding of the present invention. However, it will readily be apparent to one skilled in the art that the present invention may be practiced without these specific details.

Figure 1:
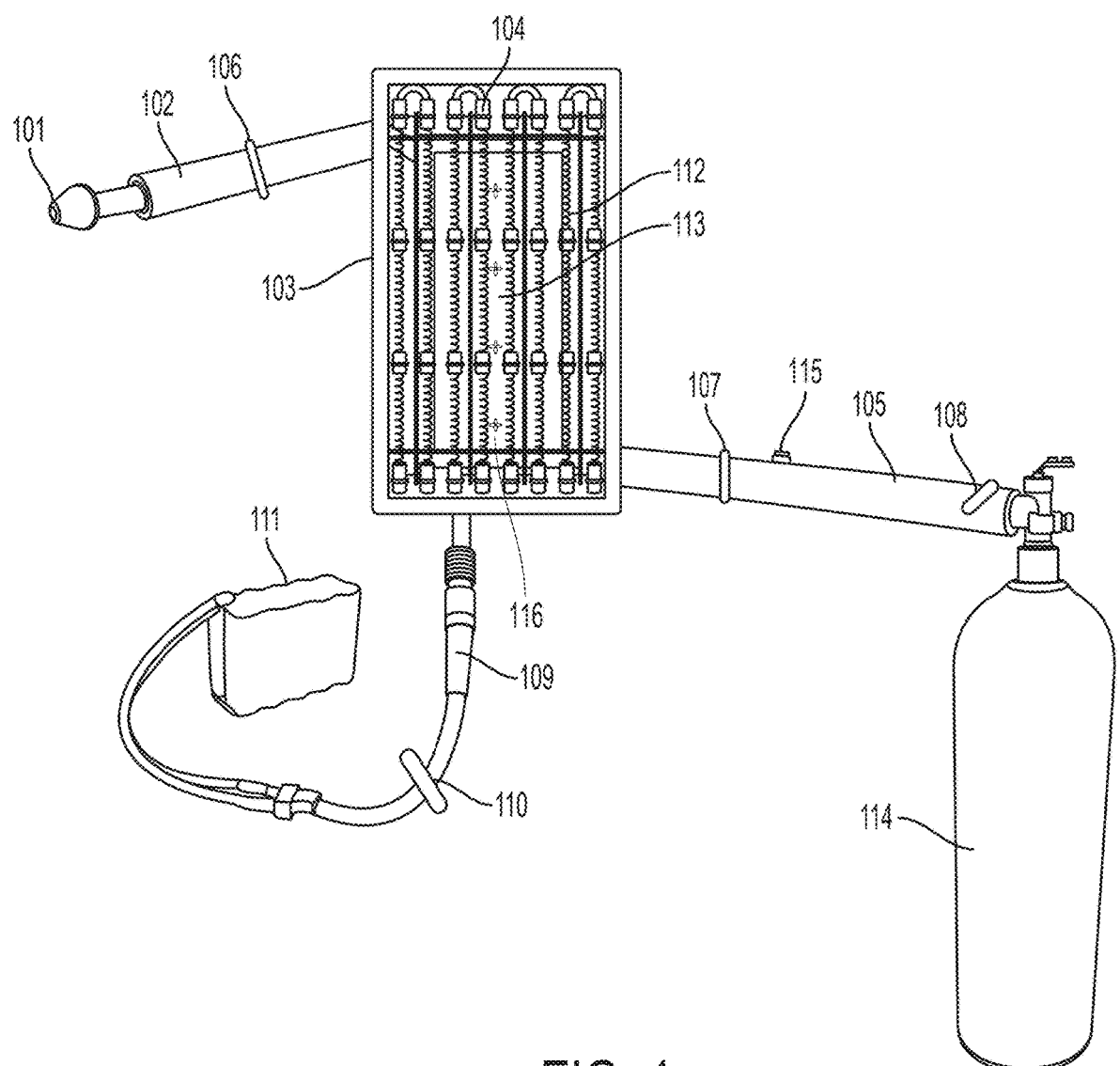
FIG. 1 is a diagram of a device for vaporizing Vaporization Targets according to an embodiment of the present invention.

Turning to FIG. 1, we note the following elements:

101: A mouthpiece suitable for breathing through.

102: Hollow tube.

103: Vaporization chamber.

104: Heating element. If resistance heating, may utilize resistors such as Nichrome or Kanthal. It may also utilize a Peltier heating device, in which case cooling elements, such as those described in 106, may (but need not) be the cool side of the Peltier heating device.

105: Hollow tube.

106: Connector between Hollow Tube 102 and Vaporization chamber 103. Connector may contain cooling elements or a valve preventing passage of gas exceeding a set temperature (although one or both of those elements may be placed at other points between the vaporization chamber 103 and the mouthpiece 101, or even integral with the mouthpiece).

107: Connector between hollow tube 105 and vaporization chamber 103. In one aspect, the connector (or valve 108 or other element between the gas container 114 and the vaporization chamber 103) may detect oxygen and warn or prevent the flow of gas.

108: Valve. Valve may be mechanical, electro-mechanical, or otherwise. In one aspect, Valve may be actuated by negative air pressure in the tube 105. In one aspect, the valve may be held closed with a spring.

109: Wiring connection (or wireless connection such as inductive charging) for power.

110: Switch (physical switch, digital switch, electromechanical or otherwise) to control power. May be controlled by microprocessor, thermistor or other temperature-sensitive switching system. May control amount of current to achieve target temperature in chamber 104.

111: Power source (direct and/or inductive).

112: (optional) pre-packed or packable container for holding plant matter (or other material for vaporization).

113: Plant matter (or other material for vaporization).

114: Gas container for holding non-oxygenated (or set amount of oxygen, or minimal amount of oxygen) gas or gas mixture. In one aspect, may be helium. In one aspect, this may be a balloon or a tank.

115: Oxygen detection mechanism

116: Chopping element

Utilizing tobacco as an example (although marijuana or other substances may also be used and the term "tobacco" should be understood to include any substance a user seeks to vaporize), and looking at FIG. 1, the device may optionally purge any extent gas from one or both of the tubing 105 and/or 102 and/or the chamber 103. It should be noted that the apparatus may be mechanically controlled, microprocessor or computer controlled, or a combination.

The user inserts tobacco into the vaporization chamber 103. In one aspect, such insertion may be via a pre-filled cartridge 112 or a removable and/or refillable cartridge 112.

Whether within a cartridge 112 or not, the tobacco 113 is inserted into the vaporization chamber 103. The user then actuates the heating element 104 (either prior to or simultaneously with other steps). The heating element 104 causes the tobacco 113 in the vaporization chamber 103 to heat. In one embodiment, the heating element is controlled by a thermistor or other mechanism for limiting the temperature of the vaporization chamber 103.

The user then actuates the valve 108. Actuation may be achieved by inhaling utilizing the mouthpiece 101, by actuating a switch 110, both, or otherwise. Once actuated, the valve 108 opens, permitting the gas stored in the gas container 114 to be released into the tube 105.

In one aspect, the connector 107 between the tube 105 and the vaporization chamber 103 may detect the presence of oxygen and cause a valve to shut (whether the valve 108 or another valve), or cause a warning to be actuated. The non-oxygenated (or minimally oxygenated gas) then passes through the heated vaporization chamber 103, transporting elements of the tobacco that have been vaporized out of the vaporization chamber 103, past the connector 106, through the tube 102, and into the mouthpiece 101 where it is inhaled by the user. While the gas in the vaporization chamber is described as non-oxygenated, said gas may, in some implementations, contain some amount of oxygen. Preferably, such a gas would contain an amount of oxygen insufficient to sustain combustion.

In one aspect, a detector between the tobacco 113 and the mouthpiece 101 (or at the mouthpiece 101) detects the presence of one or more vaporized substances. Utilizing nicotine, for example, the presence and/or concentration of nicotine in the gas flow may be measured. As the amount drops, a warning may be issued to the user that it is time to replace the tobacco 113.

In one aspect, negative air pressure must exist at valve 108 in order to open the valve, preventing the forced passage of gas through the various elements. In another aspect, a reducer may be utilized at or near valve 108 to reduce the pressure of the gas emitted from the gas container 114 to approximately equal to or slightly in excess of the ambient air pressure. Ambient air pressure may be measured utilizing a barometer or other mechanism.

In one aspect, the mouthpiece 101 may be replaced with a balloon, bag, or other container capable of storing gas. In another aspect, at the mouthpiece 101 or at any other place between the vaporization chamber and the mouthpiece 101, a temperature measuring mechanism may be utilized to warn the user, close a valve, or a combination thereof, if the gas temperature exceeds a set temperature and/or a safe temperature for inhalation. In another aspect, a cooling element may be utilized. Active cooling may be used, passive cooling such as passing through water or over ice may be used, or other forms of passive cooling such as utilizing a temperature-conductive material such as copper for part or all of the tube 102, allowing conduction of thermal energy out of the gas. A Peltier device may also be utilized, and in some cases may be desirable as it can be a source of both heating and cooling. The copper or other heat sink may extend beyond the tube 102.

In one aspect, where the vaporization target is marijuana, a vaporization temperature of 175 to 200 degrees may be utilized (it should be noted that temperatures given here are centigrade unless otherwise indicated). A vaporization temperature in excess of 200 degrees may be utilized to capture more of the organic compounds.

Because of the unique design of the system, it is possible, and in many cases desirable, to utilize a vaporization temperature in excess of 235 degrees-a temperature at which oxygenated gasses would cause the marijuana to combust, at least in part.

Similarly, tobacco, *passiflora, Turnera diffusa, Hypericum perforatum, Salvia divinorum*, and other plant products or materials may be vaporized at a temperature in excess of the normal combustion temperature in oxygenated environments.

It should additionally be noted that intermixing oxygen and/or atmospheric gas (ambient air including oxygen) may be a desirable feature. Such intermixing would occur after the vaporization takes place. It may serve to cool the gas mixture to make the temperature safer for inhalation. In addition, or in the alternative, it may serve the function of preventing the user from passing out from lack of oxygen or otherwise becoming hypo-oxygenated.

A concern is that a user of a psychoactive substance may be unable to remember to breathe oxygenated air between inhalations from a vaporization device, and may additionally be insufficiently cogent to detect hypoxia. This may lead to loss of consciousness or injury. Accordingly, a pulse oximeter or similar device may be utilized to adjust the oxygen content of air intermixed proximal to the vaporization chamber; may be used to trigger a lowering of the temperature in the vaporization chamber to below a combustion temperature, and oxygen then added to the mix fed into the vaporization chamber from the distal gas source; may be used to block further inhalation until a target and/or safe oxygen level is reached by the user. Similarly, an alarm may actuate, using vibration, sound and/or a visual signal to indicate to the user to take a breath of atmospheric air. This may be done via timer, triggered by a blood oxygen measurement, and/or triggered by a visual or audio detection of inhalation sounds. Such detection may be made utilizing a microphone operably connected to the vaporization system, whether by a near field computing connection, Bluetooth, network, wired, or other connection.

Figure 2:
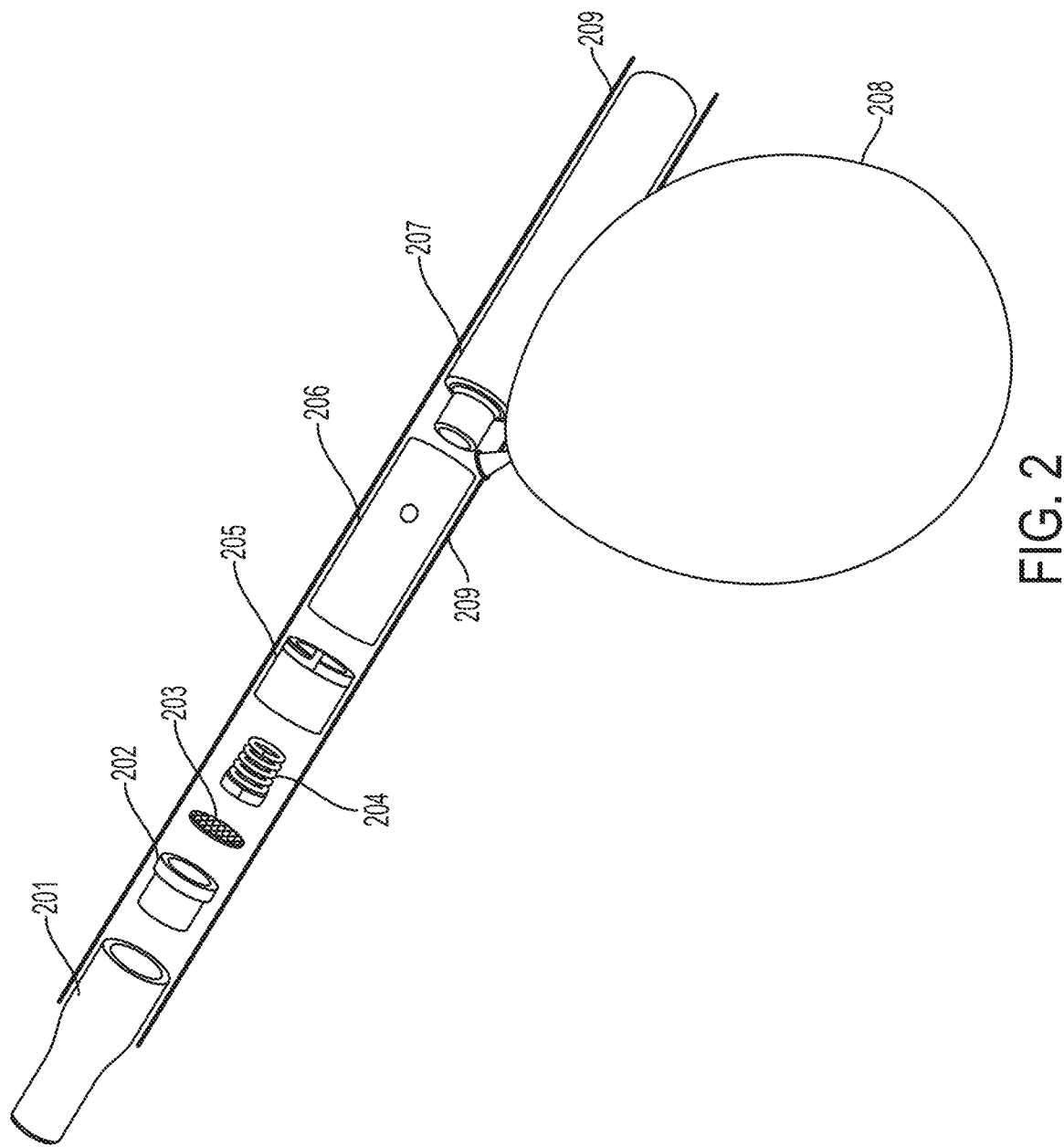
FIG. 2 is a diagram of a device for vaporizing Vaporization Targets and showing a sealant to prevent entry of atmospheric oxygen according to a second embodiment of the present invention.

Turning to another implementation, we reference FIG. 2.

FIG. 2 utilizes the vaporizer structure described in the related art section as a starting point. Distinguishing from this structure are several elements, shown and not shown. Unlike existing vaporizers, a sealant 209 is utilized to prevent oxygenated gas from entering. A gas input 209 is utilized in conjunction with a non-oxygenated (or minimally oxygenated) gas source 208 is utilized. The gas input may contain a valve. In one aspect, the valve may be actuated by negative air pressure in the chamber 206. The gas source 208 may be a balloon, a canister of gas, or another source.

Element 201 is the mouthpiece.

Element 202 is a filter to prevent plant matter from entering the lungs.

Element 203 is a filter to prevent plant matter from entering the lungs.

Element 204 is a spring.

Element 205 is a connector to couple the chamber to the filter and mouthpiece assembly. Within this element (or at any point between or including the heating chamber and the mouthpiece), a cooling element (such as water or a Peltier cooling element) and/or a valve that closes if the gas temperature is unsafe or too high, may be present.

Element 206 is the heating or vaporization chamber. In one aspect, it may be ceramic.

Element 207 is a power source.

Element 208 is a non-oxygenated gas source. A valve may be present at the connection of this element to the remainder of the system (or elsewhere between the source and the mouthpiece).

Element 209 is a sealant or sealing matter to prevent entry of atmospheric oxygen.

It should be noted that the heating chamber may be heated immediately to a temperature above combustion temperature (the combustion temperature that would exist in an oxygenated environment). Alternatively, the heating chamber may vaporize elements at a rising temperature, starting at a lower temperature and eventually reaching a temperature above combustion if there were oxygen present. In one aspect, an oxygen detection mechanism 115 is located prior to the combustion chamber (or in the combustion chamber) and prevent gas from flowing if the temperature is above a certain temperature (such as the combustion temperature for that level of oxygen). In another implementation, the rise in temperature may be regulated in a manner related to a detected amount of vapor generally, or of one of more vaporized substances. For example, as the THC level in the vapor drops, the temperature of the vaporization system rises. In one aspect, this may create a more level amount of substance in each inhalation. Gas spectrography may be utilized for a specific measurement of one or more substances. In addition, ionization and/or photoelectric sensors may be utilized to measure the amount of vapor being released. In another aspect, the weight and/or volume of the vaporization material may be measured (such as by a scale) and utilized to determine how much material is being vaporized. As the rate of reduction in weight and/or volume of material begins to slow, the temperature may be increased. In another aspect, if too much or too rapid vaporization is taking place, the temperature may be decreased.

In one aspect, the heat source may be external to the vaporization assembly. In one aspect, a copper (or other heat-conductive metal or substance) is utilized to transmit heat into the vaporization chamber.

In one aspect, a carbon monoxide detector may be utilized to detect whether combustion is taking place. In another aspect, a carbon dioxide detector may be utilized to determine whether combustion is taking place. In another aspect, detectors for combustion byproducts (such as smoke or gasses) may be utilized to determine whether combustion is taking place. In such a case, a warning may be provided, such as by a light, vibration, sound, or a combination, to the user. In another aspect, the flow of non-oxygenated gas may be increased. In another aspect, the temperature of the vaporization chamber may be reduced. In another aspect, a valve may close to prevent the user from inhaling combustion byproducts. In another aspect, a cut-off may be utilized to determine how much combustion is sufficient to trigger any of these responses.

In one aspect, a temperature measurement may be made of the gas at any point in the process after passing the vaporization chamber to determine whether the gas is a safe temperature for inhalation and/or whether the gas is a comfortable or desirable temperature for inhalation. The gas temperature may be reduced by any one or more of the cooling methods discussed herein, including Peltier, passing cooling, and intermixing with atmospheric and/or compressed gas. A valve or mechanical blocking device, and/or a warning signal, may be utilized to indicate an unsafe or potentially unsafe gas temperature.

It should be further noted that certain substances being vaporized may require one or more oxygen atoms to convert into a bioavailable state. In such a case, it may be desirable to intermix oxygenated gas at some point proximal to the vaporization chamber, the point optionally being determined by the desired temperature at which such intermixing would be efficacious.

It should be understood that in one aspect, one or more relief valves should be incorporated into the inventions. Any convention relief valve known in the art may be used.

The pressure differential between the inlet nozzle of a conventional relief valve and the outlet of the relief valve can be calculated by combining the amount of negative pressure applied to the outlet (such as by a user inhaling from the outlet) with the amount of positive pressure applied to the inlet (such as by a pressurized gas container). In one aspect, the amount of pressure differential required to open the valve should be set to be greater than the combination of ambient pressure at the outlet and helium or other non-oxygenated gas container pressure exerted on the inlet.

In another aspect, a manual or electronically coupled button or switch may be actuated by a user, opening the valve during the period it is actuated. The button or switch may be incorporated into the mouthpiece so that it is actuated by interaction with the mouthpiece, such as by biting down on the mouthpiece, closing a circuit by covering two elements of the circuit with skin, liquid, or mucous membrane, or otherwise.

In another aspect, a regulator may be utilized to convert high pressure at the gas source to a lower pressure. Such a regulator may be placed at or near element 108 in FIG. 1, or otherwise.

In another aspect, the system may operate at a pressure higher than ambient atmospheric pressure. That is, imagine that the gas source is 150 psi. Atmospheric ambient pressure is approximately 15 psi. A recipient vessel may be implemented between the heating chamber 103 and the output 101. Even after the gas source 114 is turned off, gas with vaporized elements will remain in the vessel. In another aspect, the vessel may be at approximately ambient atmospheric pressure, such as by utilizing a balloon or other container.

In another aspect, a prefilled container of plant matter 112 is utilized in conjunction with one or more elements of these inventions. The container may incorporate information about proper heating temperatures at varying pressures with varying gas and/or oxygen content within the gas. The system may utilize a microprocessor coupled with memory to read the information and control the temperature, gas flow, speed of heating, oxygen content, or a combination thereof. The microprocessor may then utilize one or more of those data points to alter the functionality of the vaporization unit. The data may be used as stored, or altered by the user.

In one aspect, unlike existing vaporizers, the instant inventions may efficiently vaporize plant matter even without grinding the plant matter, or grinding it to larger pieces than may be desirable for an existing vaporizer. In another aspect, the prefilled container 112 or inner container 112 or an element within the heating chamber, may contain a chopping element 116 (such as that present in a coffee grinder) and/or a mixing and/or tumbling and/or rotating element and/or vibratory element (any of which may be located internal to the heating chamber and some, such as the vibratory, rotating, mixing, and tumbling elements, may be located external to the heating chamber) may be utilized to break the plant matter down into smaller pieces. Such mechanisms will be particularly effective at the higher-than-combustion temperatures made possible by these inventions, as the plant matter will, in many cases, become very dry and fragile. While such mechanisms may be utilized in conventional vaporizers, the efficacy should be far higher in the instant systems.

In another aspect of the inventions, it may be desirable to incorporate a fingerprint reader, a combination code, passcode, retinal scan, other biometric measurements, or other locking means to prevent actuation of the heating element by persons not authorized to actuate it.

In another aspect of the invention, atmospheric gas, oxygenated or non-oxygenated gas, or a combination, may be utilized in a low pressure system. Because water boils when the vapor pressure reaches or exceeds the surrounding pressure, it is possible to desiccate the plant matter and make it easier to break into small, vaporization-friendly parts. Such breakage may be implemented via a chopping element 116 (such as that present in a coffee grinder) and/or a mixing and/or tumbling and/or rotating element and/or vibratory element (any of which may be located internal to the heating chamber and some, such as the vibratory, rotating, mixing, and tumbling elements, may be located external to the heating chamber) may be utilized to break the plant matter down into smaller pieces. It should be noted that this aspect may also be done independent of the vaporization systems described herein, such as in a stand-alone device.

The pressure may be alternated between low and normal and/or low and high. At the normal or high temperature, elements vaporized at the low temperature may be compressed into a holding tank, pushed out into a vessel, such as a balloon, or inhaled directly. It should be noted that a combination of heating and low pressure may result in the vaporization of additional elements when compared to the same temperature at a higher pressure, whether due to the boiling of water or otherwise.

In one aspect, the heating element may actuate, or power to the heating element may increase, or otherwise the heat may increase, when the first valve between the gas source and the system.

In another aspect, a vaporization device may be utilized in conjunction with a cigarette or other plant matter contained in a cigarette-like vessel. This is illustrated in FIG. 3.

Figure 3:
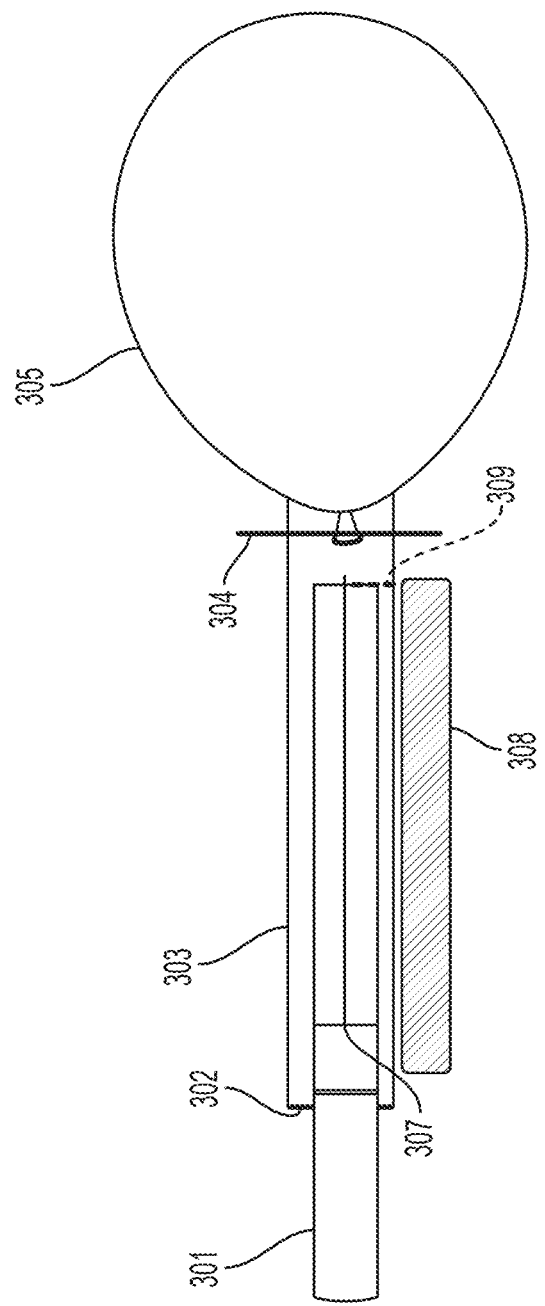
FIG. 3 is a diagram of a cigarette and a chamber that contains the cigarette that reduces the amount of atmospheric gas entering the cigarette, according to a third embodiment of the present invention.

Looking at FIG. 3, the following elements are present:
  301: A cigarette or other container holding tobacco, *cannabis*, or other substances.
  302: A sealant, such as rubber, to minimize the amount of atmospheric gas entering the system and/or to allow more efficient application of low pressure be inhaling at the end of the cigarette.
  303: A chamber that seals and/or contains the cigarette in a manner that reduces the amount of atmospheric gas entering the cigarette. In one aspect, the chamber is made of a material that minimizes heat conduction.
  304: A valve that may be used to prevent the entry of non-oxygenated or partially oxygenated gas into the system. This valve may constitute pinching the end of a balloon, a valve to a gas-containing vessel, or otherwise.
  305: A source of non-oxygenated or partially oxygenated gas.
  306: Omitted.
  307: A heating element that inserts into the plant matter within the cigarette. In one aspect, the heating element contains a sharp tip. In another aspect, the heating element is narrow. In another aspect, the heating element contains multiple prongs.
  308: A power source for the heating element. The heating element may be resistance heating. In another aspect, it may be a temperature-conductive material, such as copper.
  309: A connection between the power source and the heating element. Note that the power source may be integral with the gas source 305, the chamber 303, use inductive power, or otherwise. In another aspect, the connector may be larger or longer and composed of a heat-conductive material, such as copper, and heated directly with a heat source, such as a lighter. In such a case, the power source 308 may be a direct heat source.

As helium and other non-oxygenated gases carry an inherent risk of hypoxia, in one aspect it is desirable to provide a source of oxygen at a place in the system subsequent to the heating chamber. In one aspect, a valve is placed between the heating chamber and the inhalation point. Between the valve (or at the valve) and the inhalation point (or at the inhalation point), a source of oxygen, an oxygen gas mixture, and/or atmospheric gas is introduced. The aperture of the hole or tubing through which it is introduced may be varied to vary the mixture. In addition, whether or not a post-heating oxygenation system is in place, the system may prevent inhalation of multiple breaths or more than N breaths within a set period of time. For example, the system may allow one inhalation followed by a 30 second valve closure, followed by another inhalation and a 45 second valve closure.

In another aspect, pulse oximetry may be utilized to determine blood oxygenation, and a valve closed when blood oxygenation reaches an undesirable or unsafe level (such as below 95%) to prevent further inhalation until blood oxygenation returns to a safe or desirable level.

It should also be understood that the mechanism described in FIG. 3 may be implemented in part. For example, the heating element may be introduced without more and heated to a temperature below combustion temperature in order to vaporize the contents of the cigarette.

Further Aspects

Heating the vaporization chamber 206 to a very high temperature presents hazards to the user inhaling the highly heated vapor. In addition, a user breathing non-oxygenated gas may get carried away with utilizing the device and forget to breathe oxygenated gas between uses of the vaporization device.

In one aspect, there is a one way valve between the mouthpiece and the vaporization chamber to prevent backflow of oxygenated gas into the vaporization chamber. In another aspect, there may be a source of oxygenated gas, whether atmospheric gas or not (for purposes of this discussion, we will reference atmospheric gas, although in some aspects it may instead be compressed or non-compressed oxygenated gas not drawn from the ambient atmosphere). In most normal applications, the atmospheric gas is cooler than the vaporization temperature.

In one aspect, a compressed gas source is utilized to provide the oxygenated component and takes advantage of the cooling effect of reducing the pressure on compressed gas. In another aspect, the vaporization chamber may be pressurized. In one implementation, the distal portion of the device may be operated at the pressure of the compressed non-oxygenated gas source. In another implementation, a regulator may step down the pressure (in the case of maintaining a pressurized vaporization chamber, the regulator would step down the pressure to a pressure higher than the ambient pressure). This has the added benefits of (a) preventing the flow of oxygenated gas into the vaporization chamber, and (b) causing cooling associated with gas moving from a compressed to a less compressed state.

In another aspect, pressurized gas at the distal end may be passed through a vortex tube to heat the non-oxygenated gas prior to entry into the vaporization chamber. This may be instead of having heating elements dedicated to heating the vaporization chamber, or in addition to having such heating elements. In another aspect, the cooled air from the cold end of the vortex tube may be utilized to cool the temperature of the gas in the proximal portion of the device.

In one aspect, a vaporizer may be powered entirely by a vortex tube. In such a case, any compressed air source may be used as most substances do not combust at temperatures reached by a vortex tube (which reaches a top temperature of around two hundred degrees centigrade). In another aspect, a non-oxygenated air source may be utilized. The compressed gas entering the vortex tube may be compressed using a hand pump, an electrical pump, a compressed gas cylinder, or otherwise compressed.

Similarly, pressurized gas (whether using a pump or a compressed gas source) at the proximal end may be passed through a vortex tube prior to introduction into the post-vaporization gas flow. The cool end of the vortex tube would be a source of gas introduced to cool the post-vaporization gas flow (whether directly mixed with the post-vaporization gas or used to cool the outside of the tube through which the post-vaporization gas flows. The heated end of the vortex tube may be used to warm the vaporization chamber without intermixing oxygenated gas. For example, passing the hot gas through copper tubing within or surrounding the vaporization chamber may be desirable.

Within the proximal end of the device, oxygenated gas may be introduced through a valve-controlled intake, through an intake that can be blocked with a finger, through a filtered intake, through an intake with an aperture that is controlled (such as by a motor or valve) to obtain a desired mix of oxygenated and non-oxygenated gas (and/or to obtain a desired temperature) based on sensor data such as oximeter data, gas temperature data, vaporization temperature, flow rate of non-oxygenated gas into the distal end, flow rate of post-vaporization gas into the proximal end, or a combination.

In another aspect, a pulse oximeter (with or without the pulse measurement) or other blood oxygen measurement device may be utilized to control aspects of the device, such as valves. For example, the source of non-oxygenated gas may be sealed by a valve if the user's blood oxygen level drops more than 5% (so for example, from 100% to under 95%) and/or drops below a certain level. In another aspect, an oximeter may be operably connected to the mouthpiece and obtain measurements when the lips contact the mouthpiece.

The atmospheric gas intake should be located in the proximal area of the device in order to prevent oxygenated gas from entering the vaporization chamber.

When using oxygenated gas vaporization to release a molecule into breathable form, it is often desirable to release the maximum amount of that molecule without creating combustion byproducts. When utilizing the inventions herein, it is possible to exceed combustion temperature without creating combustion byproducts. However, this does not mean that it is always desirable to reach as high a temperature as possible. For example, it may be possible to generate plasma and utilize that as a heat source for a vaporizer, but at temperatures in the range of several thousand degrees, few organic substances will remain intact.

A further complication is that temperature control in a vaporization setting is very difficult to achieve. For example, if a heating element surrounds the inner walls of a vaporization chamber and heats the chamber to 215 degrees Celsius, the heating elements will likely need to exceed 215 degrees, while portions of the substance inside of the chamber will remain below 215 degrees. This means that even temperature-regulated vaporizers will heat unevenly. In an oxygen-present atmosphere, this may result in combustion of some elements. In the instant inventions, an optional element may be a small fan, convection, or other device that moves air within the vaporization chamber in order to better even out the temperature.

It may be desirable to increase the temperature of the vaporization chamber over the course of a vaporizing a load of material within the chamber. In one aspect, the temperature starts out at or near the boiling point and/or vaporization point for the substance the user wishes to extract from the plant material. In a further aspect, the device measures the amount of gas flowing through the chamber (which may be measured from the proximal or distal end, or from within the chamber itself). A pistol meter, oval gear meter, gear meter, helical gear meter, nutating disk meter, variable area meter, turbine flow meter, woltman meter, single jet meter, paddle wheel meter, multiple jet meter, pelton wheel, current meter, venture meter, orifice plate, dall tube, pitot tube, multi-hole pressure probe, cone meter, linear resistance meter, optical flow meter, gas source pressure meter, thermal mass flow meter, magnet flow meter, ultrasonic flow meter, Coriolis flow meter, laser Doppler flow meter, or other metering device may be utilized. As the amount of gas flow increases, the temperature of the heating elements, and thus the vaporization chamber, is increased. In this way, the amount of the desired molecule(s) being vaporized is maximized, releasing them at temperatures below the temperature where there is a risk of being denatured, gradually rising to a temperature where there may be such a risk.

In one aspect, the pressure within the vaporization chamber (and, in some aspects, within other elements of the device) is lowered, thereby lowering the boiling temperature of the molecule the user is attempting to extract. Valves and pumps may be utilized to accomplish this.

Some sources state that the vaporization temperature of THC is poorly understood, and occurs under normal atmospheric pressure at between 250-400° Fahrenheit (see http://hightimes.com/grow/what-is-the-real-boiling-point-of-thc/). Some sources list a boiling point of 392° Fahrenheit in what is essentially a vacuum (2 mm HG or approximately $\frac{1}{380}^{th}$ of one atmosphere of pressure) (see https://cameochemicals.noaa.gov/chemical/21087).

It is likely that THC aerosolizes in a vaporizer when the vaporizer is set to any of a range of temperatures. This may be due to differences in how the THC is bound to the plant matter, inconsistencies in temperature distribution, or a combination. Further, *cannabis* contains a range of chemicals that users may find desirable for medical or other purposes. These substances have a range of boiling points. See http://www.cannabis-med.org/data/pdf/2001-03-04-7.pdf. According to the same source, "traces of THC were vaporized at temperatures as low as 140° C. (284° F.) and the majority of THC vaporized by 185° C. (365° F.); benzene and other carcinogenic vapors did not appear until 200° C. (392° F.), and *cannabis* combustion occurred around 230° C. (446° F.)." The instant inventions, of course, permit heating of *cannabis* beyond the combustion temperature, allowing users to vaporize THC that is not released at the 185° C. temperature at which the study shows that a majority of THC is vaporized while avoiding any hazards or undesirable elements associated with combustion.

A study specific to vaporizers utilized a vaporizer called "the Volcano". That study "found higher temperatures more efficiently forced cannabinoids into the vapor form. Since they knew exactly how much THC their Bedrocan variety of flower had (16.9% total), they calculated the yield of cannabinoids at each temperature. At 170° C., the Volcano only yielded 24%; at 200° C. it yielded 60%; and at 230° C. the Volcano managed to put 77% of the cannabinoids from the original flower into vapor. Smoking *cannabis* in a joint only yielded 43% of the cannabinoids." (see http://hightimes-.com/grow/studying-the-vaporizer-insight-into-proper-vape-use/).

Smoke Control Device

Figure 4:
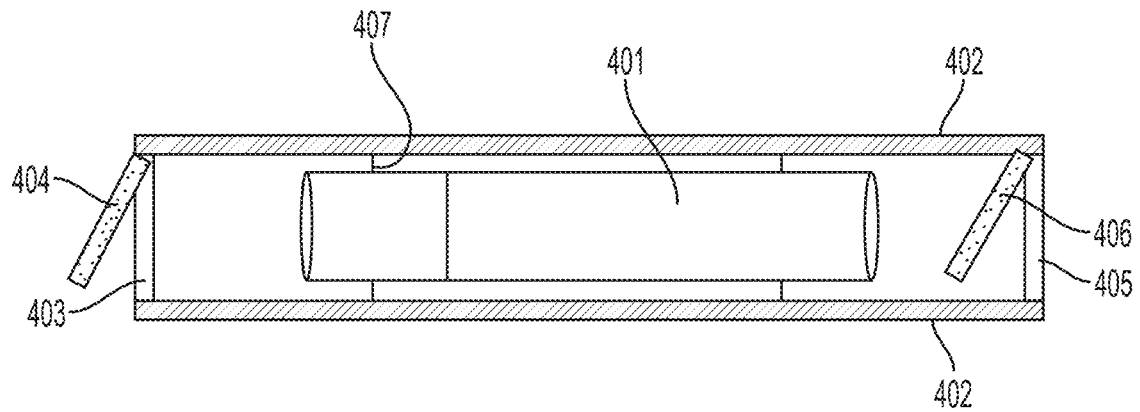
FIG. 4 is a diagram of a cigarette in an air-tight enclosure with one-way valves at the ends of the enclosure according to a fourth embodiment of the present invention.

For some people and in some situations, it is desirable to combust or vaporize material in a manner that releases a minimal amount of smoke and/or odors. It should be noted that most people associate the smells of substances burned or vaporized in an oxygenated environment with the substance, and certain substances may smell differently, if at all, when vaporized in a non-oxygenated environment. Turning to FIG. 4:

401 is a cigarette, whether comprising tobacco, *cannabis*, other materials, or a combination.
402 is a substantially air-tight enclosure.
403 and 405 are one-way valves in a closed position.
404 and 406 are one-way valves in an open position.
407 is a connection to hold the cigarette in place in the device.

Note that valve 405 406 may be capable of being locked into an open position for purposes of lighting the cigarette. Similarly, a combustion or heat source may be located within the enclosure, for example between the end of the cigarette and valve 405 406. If a heat source other than combustion is used, a non-oxygenated gas source may be connected to the end of the enclosure 402, such as near valve 405 406.

Using this enclosure, fumes from the cigarette are contained within the enclosure when the cigarette is not being smoked or vaporized.

Of course, smoke or vapor that has been inhaled presents a problem upon exhalation. This may be solved utilizing the inventions described in FIG. 5.

501 is a substantially airtight enclosure.
502 and 504 are one way valves in a closed position. Note that both valves are optional.
503 and 505 are one way valves in an open position.
506 is a filter.

Optionally, a receptacle, such as a balloon, may be affixed to the device near the end (near positions 504 505).

Figure 5:
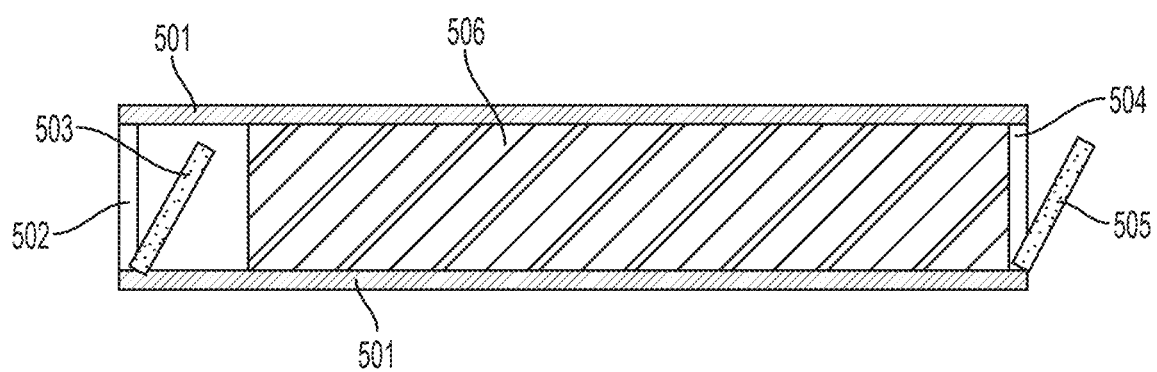
FIG. 5 is a diagram of a filter inside of an air-tight container with one-way valves at the ends of the container, according to a fifth embodiment of the present invention.

The devices shown in FIGS. 4 and 5 may be utilized in combination, thereby capturing the majority of the odor prior to and during inhalation (FIG. 4) as well as during exhalation (FIG. 5).

In one aspect, the devices of FIGS. 4 and 5 may be operably combined or connected.

For example, a single enclosure may be utilized whereby the valve at the mouth end (502 503 403 404) is a two-way valve. When inhaling, the valve opens in a manner that closes access to the FIG. 5 portion of the device and opens access to the FIG. 4 portion of the device. Upon exhalation, the valve to the FIG. 5 portion opens and the valve to the FIG. 4 portion closes. In another aspect, two one-way valves may be utilized to obtain similar functionality.

The shapes of the FIG. 4 and FIG. 5 portion need not be circular. Indeed, in one aspect the filter portion shown in FIG. 5 may be deployed on the exterior of the substantially airtight chamber 402 of FIG. 4. In this manner, a user may inhale and exhale through the same hole. Similarly, a single mouthpiece may be utilized, simultaneously connected to both the FIG. 4 and FIG. 5 apparatus.

Recycling of Active Ingredients

It is common for byproducts of smoking to accumulate on parts of devices used to smoke. For example, a metal filter in a bong or vaporizer, the mouthpiece of a vaporizer, or other parts may accumulate nicotine (in the case of tobacco) or THC or other cannabinoids (in the case of *cannabis*).

Using THC and a vaporizer as an example, it is common for THC to accrue on various parts. For example, using a pen vaporizer such as the one illustrated above, and utilizing a concentrate such as *cannabis* wax as the THC source, THC will accrue around the heat source and elsewhere in the mechanism. A standard way to clean these parts is to immerse them in alcohol, which dissolves the THC.

The parts can be cleaned by heating them, causing the THC to boil off as a gas. By utilizing a vaporizer with a large enough heating chamber, it is possible to utilize what would otherwise be waste THC by placing them in the chamber. For parts that are flammable, such as a paper filter, utilizing a non-oxygenated atmosphere (as described above) is an effective way to utilize the THC without creating additional combustion byproducts. The vaporization discussed herein may be for organic, biochemical, inorganic, psychoactive, non-psychoactive, volatile organic, and/or other products.

It should be noted that the source of non-oxygenated gas may be actuated by computer, by manual operation, by a valve actuated by the creation of a partial vacuum (in the vaporization chamber, in the distal tube or conduit, or in any other place between the proximal tube and the source of non-oxygenated gas), or otherwise.

It should further be noted that the shape of the vaporization chamber may be designed such that a cigarette or cigarette-shaped object may be placed in the chamber.

The described systems and processes merely exemplify various embodiments of enhanced features. The present technology is not limited by these examples.

The invention claimed is:

1. A device for vaporization of compounds comprising:
   a vaporization chamber for placement of the compounds, the vaporization chamber sealed during operation of the device, except for at least two conduits;
   the vaporization chamber having a receptacle for the compounds;
   a first conduit of the at least two conduits operably coupled to a first source of a first gas having a set amount of oxygen;
   where the first gas is a compressed gas delivered at above ambient pressure;
   a heating element capable of heating the vaporization chamber to a temperature above an upper temperature limit for vaporization that avoids combustion;
   a second conduit of the at least two conduits, the second conduit configured to transport vaporized elements of the compounds out of the vaporization chamber; and
   an oxygen detection mechanism located upstream of the vaporization chamber preventing the first gas from entering the vaporization chamber if the temperature in the vaporization chamber is above a threshold temperature for a level of oxygen in the first gas.

2. The device of claim 1, wherein the set amount is substantially non-oxygenated.

3. The device of claim 1, wherein the first gas is helium.

4. The device of claim 1, wherein the first gas is nitrogen.

5. The device of claim 1, wherein the first gas is argon.

6. The device of claim 1, wherein a cooling element is downstream of the vaporization chamber, the cooling element configured to cool gas passing through it.

7. The device of claim 6, wherein the cooling element comprises piping.

8. The device of claim 1, wherein the heating is accomplished, at least in part, using resistance heating.

9. The device of claim 1, wherein the set amount is an amount of oxygen insufficient to sustain combustion.

10. The device of claim 1, wherein the receptacle contains unground *cannabis*.

11. The device of claim 1, where a valve is present at the connection of the first gas source to a remainder of the system.

12. The device of claim 1, where oxygenated gas is intermixed with the vaporized elements downstream of the vaporization chamber.

13. The device of claim 1, where one or more of a combination code, passcode, retinal scan, fingerprint scan, or other biometric measurement is required prior to actuation of the heating element.

14. The device of claim 1, where an intake is present in a portion of the device downstream of the vaporization chamber, which intake provides a source of atmospheric oxygen and is controlled by blocking the intake with a finger.

15. The device of claim 1, where the temperature in the vaporization chamber gradually rises to a temperature where there is a risk of denaturing one or more of desired molecules being vaporized.

16. The device of claim 1, where portions of plant matter that accumulate on parts of devices used to aerosolize plant matter are heated within the device to a temperature where some or all of those portions of plant matter become aerosolized.

17. A device for vaporization of compounds comprising:
a vaporization chamber for placement of the compounds, the vaporization chamber sealed during operation of the device, except for at least two conduits;
the vaporization chamber containing unground *cannabis* flower;
a first conduit of the at least two conduits operably coupled to a first source of a helium gas;
where the helium gas is compressed and delivered at above ambient pressure;
a heating element capable of heating the vaporization chamber to a temperature above the upper temperature limit for vaporization that avoids combustion;
a second conduit of the at least two conduits, the second conduit configured to transport vaporized elements of the compounds out of the vaporization chamber; and
a chopping element internal to the vaporization chamber to break down the *cannabis* flower into smaller pieces.

* * * * *